(12) United States Patent
Jamison et al.

(10) Patent No.: US 11,060,399 B2
(45) Date of Patent: Jul. 13, 2021

(54) DRILLING WITH CUTTINGS DENSITY CALIBRATION

(71) Applicant: Halliburton Energy Services, Inc., Houston, TX (US)

(72) Inventors: Dale E. Jamison, Humble, TX (US); Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 88 days.

(21) Appl. No.: 16/606,533

(22) PCT Filed: Nov. 29, 2017

(86) PCT No.: PCT/US2017/063781
§ 371 (c)(1),
(2) Date: Oct. 18, 2019

(87) PCT Pub. No.: WO2019/108183
PCT Pub. Date: Jun. 6, 2019

(65) Prior Publication Data
US 2021/0115789 A1 Apr. 22, 2021

(51) Int. Cl.
| | |
|---|---|
| *E21B 49/00* | (2006.01) |
| *E21B 21/01* | (2006.01) |
| *E21B 44/00* | (2006.01) |
| *G01N 9/36* | (2006.01) |
| *G01N 33/28* | (2006.01) |

(52) U.S. Cl.
CPC ............ *E21B 49/005* (2013.01); *E21B 21/01* (2013.01); *E21B 44/00* (2013.01); *G01N 9/36* (2013.01); *G01N 33/2823* (2013.01); *E21B 2200/20* (2020.05)

(58) Field of Classification Search
CPC .............................. E21B 49/005; E21B 49/00
See application file for complete search history.

(56) References Cited

U.S. PATENT DOCUMENTS

| 2011/0203845 A1 | 8/2011 | Jamison et al. | |
| 2011/0255994 A1* | 10/2011 | Field ....................... | F04C 18/16 417/53 |

(Continued)

OTHER PUBLICATIONS

ISRWO International Search Report and Written Opinion for PCT/US2017/063781 dated Aug. 27, 2018.

*Primary Examiner* — Kristyn A Hall
(74) *Attorney, Agent, or Firm* — Tenley Krueger; C. Tumey Law Group PLLC

(57) ABSTRACT

A drilling operation can be optimized based on feedback provided by density sensors in a flow pipe. The drilling can be in a wellbore penetrating a subterranean formation while circulating a drilling fluid. The sensor can be used to detect an actual density of cuttings in the drilling fluid and within a region of the flow pipe. A modelled density of the cuttings can be calculated for the region based on an initial model. The initial model can be based on a comparison of an equivalent circulating density profile to a fracture gradient of the subterranean formation. Based on a comparison of the actual density of the cuttings to the modelled density of the cuttings, the initial model can be adjusted to generate an adjusted model. At least one operational parameter of the drilling can be changed based on the adjusted model.

17 Claims, 6 Drawing Sheets

(56) References Cited

U.S. PATENT DOCUMENTS

2013/0180330 A1 7/2013 Gao et al.
2014/0202772 A1 7/2014 Kulkarni et al.
2015/0070000 A1 3/2015 Gao et al.
2016/0245048 A1 8/2016 Jamison et al.
2017/0131429 A1 5/2017 Schneider
2019/0212238 A1 7/2019 Gao et al.

* cited by examiner

DRILLING WITH CUTTINGS DENSITY CALIBRATION

TECHNICAL FIELD

The present description relates in general to optimizing drilling operations, and more particularly to, for example, without limitation, calibration of drilling models with calibration based on measurements of cuttings density.

BACKGROUND OF THE DISCLOSURE

Once a prospective reservoir of oil or natural gas in a subterranean formation has been located a drilling rig can be set up to drill a wellbore penetrating the subterranean formation. The drilling rig generally includes power systems, mechanical motors, a rotary turntable drill, and/or a circulation system that circulates drilling fluid, sometimes called "mud," throughout the borehole. The fluid serves to remove materials, sometimes called "cuttings," as the drill bit loosens them from the surrounding rock during drilling and to maintain adequate wellbore pressure.

At least some drilling operations involve rotating a drill bit at the distal end of the pipe, sometimes called "drill string," and transmitting rotary motion to the drill bit using a multi-sided pipe known as a "kelly" with a turntable. In other drilling operations, the drill bit is rotated with a motor near the drill bit such that the drill string does not rotate. In both cases, as drilling progresses, drilling fluid circulates through the pipe and out of the drill bit into the wellbore. At least a portion of the cuttings are removed from the wellbore by the circulating drilling fluid. New sections may be added to the pipe progressively as the drilling continues to extend the drill bit further into the subterranean formation. Once a desired depth is reached, drilling is completed. Various tests can be conducted at this point to precisely locate and isolate portions of the formation housing the desired hydrocarbon deposits.

Drilling operations can be expensive and time consuming. Therefore, increasing drilling efficiency or productivity, even to a small degree, can lead to significant monetary savings.

The efficiency of a drilling operation is generally determined by the ratio of productive rig time (e.g., time spent drilling) ("PRT") to non-productive time ("NPT"). During a drilling operation, it is desirable to maximize this ratio because NPT has a cost with minimal to no associated payout. Further, it is desirable to minimize the total time (i.e., PRT plus NPT) to minimize costs.

Minimizing rig time may be achieved by increasing the rate of penetration of the drill bit through the subterranean formation without the equivalent circulating density ("ECD") exceeding the fracture gradient. Generally, the fracture gradient (which varies along the length of the wellbore) is the pressure at which the formation will fracture, and the ECD is a measure of the pressure that the drilling fluid exerts on the formation. When the ECD exceeds the fracture gradient, the formation will fracture. Unintentional fracturing of the formation can lead to lost circulation that may require remedial operations that contribution to NPT.

Figure 1:
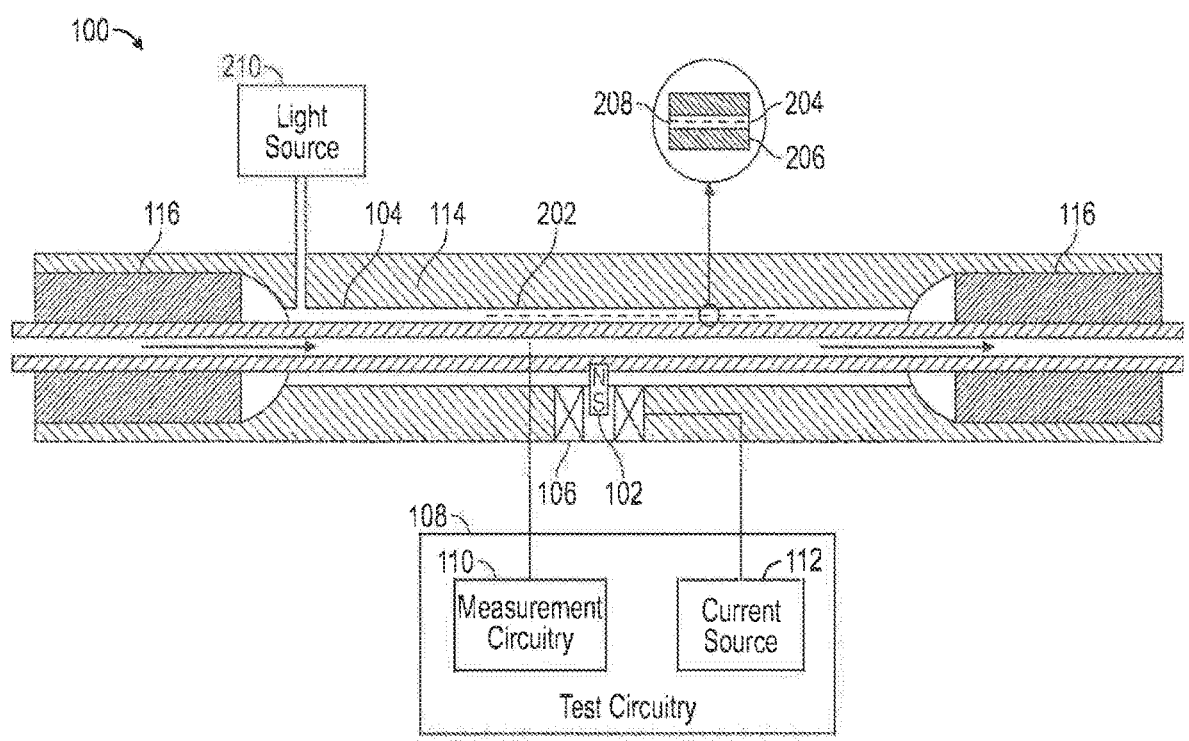
FIG. 1 is a sectional view of a distributed acoustic sensing device for measuring a density of a fluid in a flow pipe, according to some embodiments.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

In some instances, modeling programs based on steady-state approximations are used to estimate the ECD and compare it to the fracture gradient. Steady-state approximations typically use an average of the drilling parameters/operations and apply those averages to determining an ECD at any point during drilling. For example, well cleaning during a drilling operation may average about 2-8 minutes and be performed on average every 30-60 minutes. During well cleaning, drilling ceases, so further cuttings are not produced. This can alter the concentration of cuttings in the drilling fluid. Steady-state approximations of ECD would not take into account such changes during well cleaning. This example can be extended to other drilling parameters including rate of penetration into the subterranean formation, length of connection times, and RPM variations for the drill bit. Collectively, these parameters can introduce varying levels of error into the modeling program. One way to account for these potential errors is to drill at an ECD sufficiently lower than the fracture gradient to mitigate formation fracture and resultant fluid loss and lost circulation. However, this approach can reduce the efficiency of a drilling operation.

The systems and methods described herein can use drilling simulations that advantageously include inputs from real-time data and a transient model of the cuttings distribution along the wellbore. This transient modeling of the cuttings based on real-time data provides a more accurate ECD profile in the wellbore than steady state models, which allows for operating closer to the fracture gradient with less risk of formation fracture, thereby mitigating NPT. Closer operation to the fracture gradient facilitates increasing rate of penetration, which reduces the PRT.

Further, the systems and methods described herein may be configured, in some embodiments, to use a drilling simulator to predict the ECD in response to theoretical changes in the operational parameters (e.g., trajectory of the drill bit, properties of the drilling fluid, and rate of penetration into the subterranean formation). The operational parameter changes may bring the ECD closer to the fracture gradient when implemented, which may increase the efficiency of the drilling operation. Further, the operational parameters that may cause the ECD to exceed the fracture gradient may be avoided, thereby mitigating NPT.

The drilling simulator can manage and track the volume of cuttings produced during drilling and reaming. Additionally, the drilling simulator can predict when the cuttings will clear the wellbore and the ECD with the cuttings. Without knowing when cuttings actually clear the wellbore, uncertainties can be introduced into the ECD modeling. The systems and methods described herein provide feedback to refine and calibrate the cuttings transport models in real time, providing the ability to operate the wellbore ECD much closer to the fracture gradient than previously possible.

The systems and methods described herein can be used to monitor the cuttings mass flux at the flow line in real time and use this information to calibrate/improve cuttings transport algorithms resulting in better rate of penetration ("ROP") optimization and ECD management. This facilitates matching or tuning the cuttings transport modeling to actual field conditions and cuttings characteristics (e.g., size distribution and aspect ratio) that are attributed to weight on bit ("WOB"), ROP, bit type, and lithology. The transport efficiency factors that are calculated for different drilling scenarios and workflows can be cataloged and used in drilling simulator scenarios for planning.

The systems and methods described herein can be used to provide early kick detection without the need to monitor pit levels. Additionally, in managed pressure drilling ("MPD"), a series of sensors will provide better modelling and control parameters to manage the ECD. The systems and methods described herein can provide real time cuttings transport modelling, improved ECD accuracy, cuttings attrition rate estimates, and wellbore caving detection.

According to some embodiments, while drilling a wellbore, real-time data may be collected. Examples of real-time data to be collected may include, but are not limited to, flow rate of the drilling fluid, viscosity of the drilling fluid, density (or weight) of the drilling fluid, revolutions per minute of the drill bit, rate of penetration into the subterranean formation, torque applied to the drill string, trajectory of the drill bit, weight on bit (e.g., for calculating characteristics of the cuttings produced during drilling), measured depth, true vertical depth, formation composition (e.g., for calculating wellbore stresses and time-dependent fracture gradients), temperature (e.g., for calculating fluid viscosity changes), pressure (e.g., for calculating expansion and contraction of fluids), and the like, and any combination thereof. As used herein, the term "measured depth" refers to the length of the wellbore, which depending on the trajectory of the wellbore may be equal to or greater than the true vertical depth. As used herein, the term "true vertical depth" refers to the depth of the wellbore measured in a straight line perpendicular to the surface.

The real-time data collected during the drilling operation may be measurements from sensors in the wellbore, sensors in the drill bit, sensors along the drill string, sensors at the well head, sensors in wellbore tools on the drilling rig (e.g., shakers and pumps), and the like, and any combination thereof. One of ordinary skill in the art with the benefit of this disclosure would recognize the types of sensors that can be employed for the desired measurement (e.g., temperature sensors, pressure sensors, flow rate sensors, viscometers, and the like).

In some instances, the real-time data may be calculated from such measurements. For example, ECD may be calculated based on, inter alia, the measured viscosity of the drilling fluid, wellbore pressure, and the like. In another example, the morphology, density changes, and attrition size and rate of the cuttings may be calculated from fluid composition, formation composition, shear history, and tortuosity of the wellbore. These properties of the cuttings would affect the distribution of the cuttings in the wellbore because these properties affect the transport of cuttings through the wellbore (e.g., transportation rates, settling rates, and the like).

Using the real-time data or a portion thereof as an input, a transient model may be used to calculate the cuttings distribution along the length of the wellbore produced during drilling. In some instances, drilling operations are halted briefly such that the drilling fluid is no longer circulating (e.g., during NPT). The transient model may, in some instance, be capable of calculating the cuttings distribution along the wellbore taking into account settling of the cuttings during the NPT.

Calculating the cuttings distribution (i.e., distribution of cuttings along the wellbore or a portion thereof) may be achieved with a transient model that takes into consideration a plurality of factors that affect the amount of cuttings produced and their transport up and out of the wellbore. The real-time data described herein may be used as inputs to the transient model. For example, a higher viscosity fluid may reduce settling of the cuttings when the flow rate of the drilling fluid is reduced or stopped. Further, at higher temperatures, the cuttings may settle more quickly when the flow rate of the drilling fluid is reduced or stopped. As the temperature typically varies along the length of the wellbore, the settling rate of the cuttings at various points or sections along the wellbore may vary. Further, as the cuttings travel through the wellbore, attrition occurs, which changes the size, shape, and concentration of the cuttings. In some instances, cuttings attrition may be accounted for in the transient model. Transient models described herein would include several inputs from real-time data to produce a cuttings distribution.

According to some embodiments, measurements can be taken to facilitate calibration a model of the drilling simulator. FIG. 1 shows a sensor device 100 for measuring a density of a fluid according to some embodiments. The density can be measured within a region of a flow pipe 104 based on distributed acoustic sensing ("DAS") performed by the sensor device 100.

Figure 2:
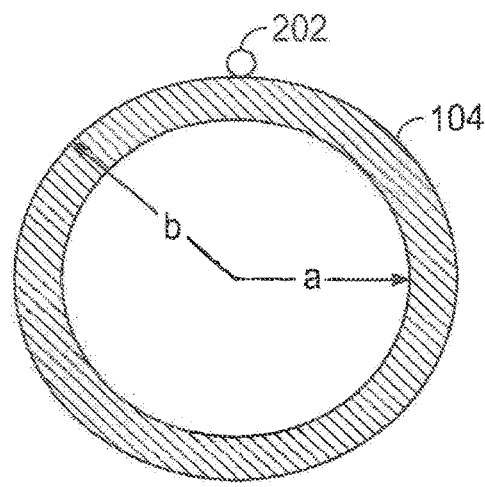
FIG. 2 is another sectional view of the distributed acoustic sensing device of FIG. 1 on the flow pipe, according to some embodiments.

The sensor device 100 can include a magnet 102 coupled to a flow pipe 104. As shown in FIG. 2, the flow pipe can have an inner radius, a, and an outer radius, b. A coil 106 can be wound around the magnet 102 and coupled to test circuitry 108, which includes measurement circuitry 110 and current source 112. The sensor device 100 can also include a rigid housing 114 and two bulkheads 116. Rigid housing 114 surrounds and protects a volume through which flow pipe 104 passes and reduces the response to vibrations not associated with particular vibratory modes of flow pipe 104. The bulkheads 116 seal the volume and secure flow pipe 104 within that volume.

One mechanism for performing distributed acoustic sensing is with a fiber optic sensor 202, as shown in FIG. 1. The fiber optic sensor 202 can be a fiber Bragg grating, which includes a fiber optic core 204 surrounded by a fiber optic cladding material 206 with a Bragg grating 208 enclosed in a portion of the fiber optic core 204. In use, the magnet 102 and the coil 106 can act as a vibration source. The current source 112 provides a current pulse to the coil 106, generating an electromagnetic force that interacts with the magnet 102 and causes flow pipe 104 to vibrate. The Bragg grating 208 can act as a period or aperiodic perturbation of the effective refractive index in the fiber optic core 204. The refractive index perturbation results in a reflection of light propagating through the fiber optic sensor 202 from light source 210 in a narrow range of wavelengths, for which the following Bragg condition is satisfied:

$$\frac{2\pi}{\Lambda} = 2\frac{2\pi\eta_{eff}}{\lambda} \Rightarrow \lambda = 2\eta_{eff}\Lambda, \quad \text{(Eq. 1)}$$

where $\Lambda$ is the grating period, $\lambda$ is the vacuum wavelength, and $\eta_{eff}$ is the effective refractive index of light in fiber optic sensor 202. The wavelength $\lambda$ of maximum reflectivity (or Bragg wavelength) depends on the grating period $\Lambda$ as well as temperature and mechanical strain, as both of these factors influence the effective refractive index $\eta_{eff}$ of the Bragg grating 208 and thus produce changes in the light that is transmitted through or reflected back in fiber optic sensor 202. As the flow pipe 104 vibrates, it also bends, which creates mechanical stress along the length of the flow pipe 104. This mechanical stress will influence the effective refractive index $\eta_{eff}$ of Bragg grating 208 and thus produce changes in the light that is transmitted through the fiber optic sensor 202. Consequently, the measurement circuitry 110 can include an optical sensor that is able to detect these changes and use the changes of light to determine the mechanical stress of flow pipe 104 from the vibration of flow pipe 104 to determine a resonance frequency of flow pipe 104. The density of the fluid flowing through flow pipe 104 can then be determined from the determined resonance frequency. Further, the measurement circuitry 110 can further analyze the temporal decay rate of the voltage to determine a Q-factor of the fiber optic sensor 202. Then, the determined Q-factor can be used to determine viscosity of the fluid flowing in the flow pipe 104.

According to some embodiments, the measurement circuitry 110 may include a spectral analyzer configured to perform a specific transform on the time-based output. Alternatively or in combination, the measurement circuitry 110 may include a processor configured to execute instructions stored in a memory coupled to the processor to perform a specific transform on the time-based function and then execute further instructions stored in the memory to calculate a fluid density from a resonance frequency determined from the specific transform. Alternatively or in combination, the measurement circuitry 110 can include application specific circuitry configured to perform a specific transform, determine a resonance frequency, and then determine a fluid density from the determined resonance frequency. Furthermore, the measurement circuitry 110 can also include components capable of calculating further properties of the fluid, such as viscosity of the fluid.

Alternatively or in combination, the vibrations can be measured by other mechanisms. For example, after the current pulse has been applied, the vibration in flow pipe 104 can move the same magnet 102 within the coil 106 or a different magnet within a different coil, therefore creating a voltage. The voltage is detected as it varies over time and provides the detected voltages to measurement circuitry 110. From the provided voltages, measurement circuitry 110 can calculate a fluid density of the fluid in flow pipe 104. In some embodiments, measurement circuitry 110 performs an operation on the provided voltages and determines a resonance frequency of flow pipe 104.

Other mechanisms for measuring vibrations can be provided. For example, as described in U.S. Patent Publication No. 2015/0070000, a fiber optic device, a metallic wire, a strain gauge, and/or an electric hammer can be used as a vibration detector. The entirety of U.S. Patent Publication No. 2015/0070000, including description of these mechanisms used as a vibration detector, is hereby incorporated herein by reference, as if fully set forth herein.

According to some embodiments, the sensor device 100 can be used as a temperature sensor for performing distributed temperature sensing ("DTS"). When a light pulse propagates along the fiber optic sensor 202, the light pulse interacts with materials of fiber optic sensor quantum mechanically to produce two types of Raman scattering: Stokes scattering and anti-Stokes scattering. Stokes scattering is independent of temperature, but anti-Stokes scattering latter is temperature-dependent. By measuring the ratio of intensity of the anti-Stokes scattering to Stokes scattering, a local temperature of the fiber optic sensor 202 and thus, the flow pipe 104, can be determined.

Other mechanisms for measuring temperature can be provided. For example, as described in U.S. Patent Publication No. 2013/0180330, a fiber optic device and/or a strain gauge can be used as a temperature detector. The entirety of U.S. Patent Publication No. 2013/0180330, including description of these mechanisms used as a temperature detector, is hereby incorporated herein by reference, as if fully set forth herein.

Figure 3:
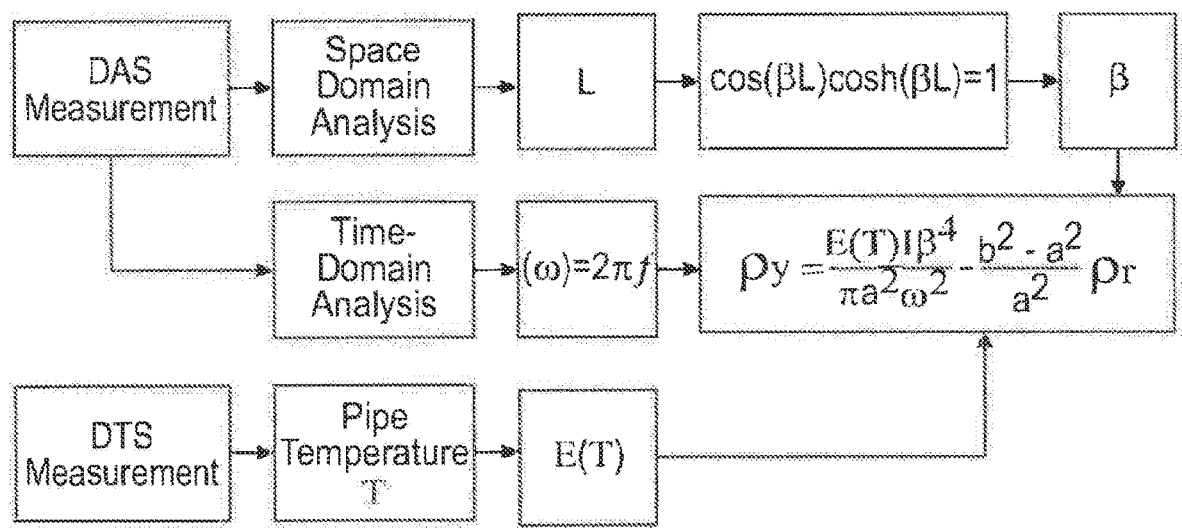
FIG. 3 is flow chart illustrating a process for obtaining fluid density from distributed acoustic sensing data and distributed temperature-sensing data, according to some embodiments.

According to some embodiments, a process can be employed for obtaining fluid density from DAS data and DTS data. FIG. 3 shows an exemplary flow chart illustrating operational steps, which are described further herein. As shown, inputs of the operations include DAS data and DTS data, which can be obtained for each of one or more regions of the flow pipe 104, as described above.

The frequency of the vibration will depend on the density $\rho_F$ of the fluid inside the flow pipe 104, the dimensions of the flow pipe 104, the density of the flow pipe 104, and the temperature dependent Young's modulus E(T) of the flow pipe 104. By analyzing the DAS data in time and space domains, fluid density can be determined.

From Euler's beam theory, it can be shown that the transverse vibration of a pipe carrying fluid is governed by the following differential equation:

$$E(T)I\frac{\partial^4 y(x,t)}{\partial x^4} + (m_P + m_F)\frac{\partial^2 y(x,t)}{\partial t^2} = 0, \quad \text{(Eq. 2)}$$

where:
the pipe's linear density is $m_P = \pi(b^2 - a^2)\rho_P$
the linear density of the fluid is $m_F = \pi a^2 \rho_F$,
the area moment of inertia of the pipe is $$I = \frac{\pi}{4}(b^4 - a^4),$$

and
the transverse displacement of the pipe at position x at time t is y(x, t).

The flow pipe can have an inner radius, a, and an outer radius, b (see FIG. 2). Assuming a separation of the temporal and spatial variables, and a time harmonic solution exp(iωt) with ω=2πf, where f is the pipe vibration frequency, the general solution of the differential equation in the spatial variable is $$y(x) = c_1 \sin(\beta x) + c_2 \cos(\beta x) + c_3 \sinh(\beta x) + c_4 \cosh(\beta x), \quad \text{(Eq. 3)}$$

where $$\beta^4 = \frac{(m_P + m_F)\omega^2}{E(T)I}. \quad \text{(Eq. 4)}$$

The value of β is determined by boundary conditions on the pipe. For example, for a simply supported pipe at two ends, the characteristic equation for β is $$\cos(\beta L)\cosh(\beta L) = 1 \quad \text{(Eq. 5)}$$

where L is the distance between the nodes of the first mode obtained from DAS data. From Eq. 4, β is obtained via standard numerical algorithms for root-finding, such as the secant method. Once β is known, Eq. 5 is used to solve for fluid density:

$$\rho_F = \frac{E(T)I\beta^4}{\pi a^2 \omega^2} - \frac{b^2 - a^2}{a^2}\rho_P. \quad \text{(Eq. 6)}$$

Since a pipe's Young's modulus E is a function of temperature, the temperature can be measured and used in Eq. 6. This can be achieved by a fiber optic device and/or another temperature sensor as described herein. The functional form of E(T) can be predetermined and stored as a look-up table, or it can be reduced into analytic form using nonlinear curve fitting routines or algorithms such as Eureqa.

Figure 4:
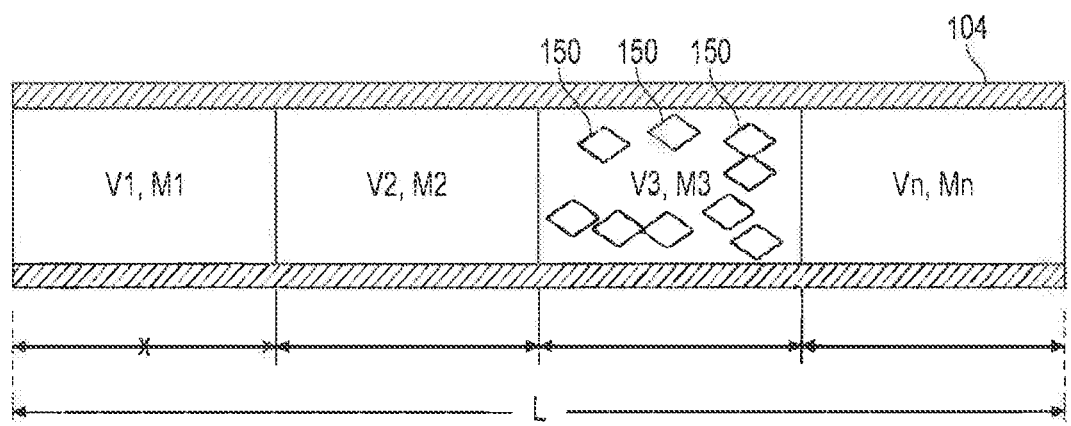
FIG. 4 is schematic diagram of cuttings within a flow pipe, according to some embodiments.

Knowing the mass/density with respect to time within the sensor element and the volume flow rate, the volume of cuttings that are passing through the sensor can be determined. For example in FIG. 4, the length of the cuttings transport sensor has n volume elements, $V_i$, with their discrete position known as well as their mass, $M_i$, with respect to time. The measurements can be refined to consider one or more volume elements. When multiple cutting volume elements enter the sensor, an averaged response, such as a mass volume cumulative of the volume elements, can be measured. The sensor output would be a single density value corresponding to the entire mass in that section of pipe.

According to some embodiments, techniques described herein are used to measure cuttings by examining a difference between drilling fluid density entering the drill string on the inlet side and drilling fluid density exiting the drill string at the outlet side. The density reading from the sensor is the cumulative mass of both drilling fluid and cuttings. The information regarding the cuttings can be extracted with knowledge of drilling fluid density.

Characteristics of the contents in the drilling fluid can be inferred from this technique. For example, solid content, such as sand, can be detected from the method described above. Such a detection can be recorded and transmitted to a user or a program. Predefined alerts and actions can be performed based on the detection.

Figure 5:
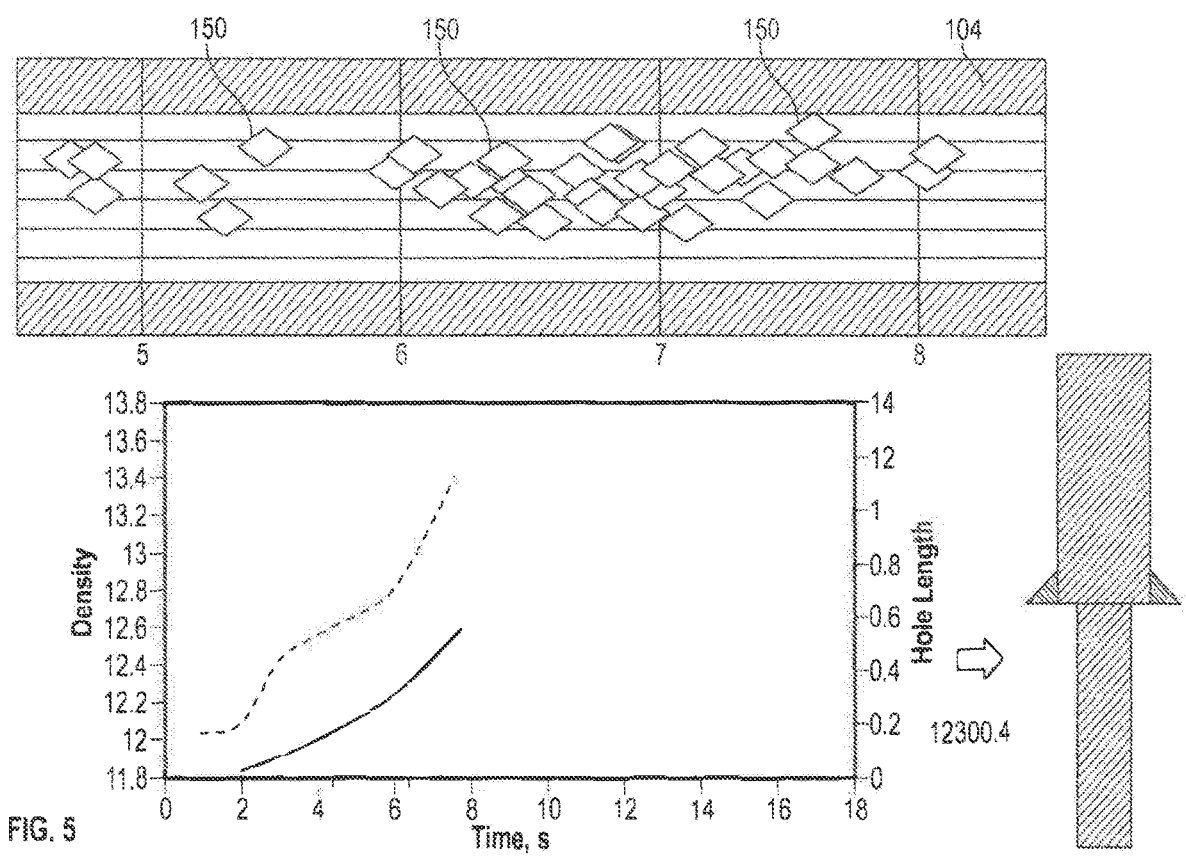
FIG. 5 is schematic diagram of cuttings within a flow pipe and a chart showing (1) a density of the bulk fluid going through the sensor with respect to time and (2) the hole depth increase that would account for the measured cuttings mass (and volume) and that corresponds to a certain measured depth change, according to some embodiments.

According to some embodiments, the mass (and density) vs time response can be calculated and/or plotted based on the process described above. The cutting flux can be plotted in real time and correlated to an increase in hole depth. For example, as shown in FIG. 5, discrete cuttings are in the density sensor. The upper plot in FIG. 5 shows the density of the bulk fluid going through the sensor with respect to time. The lower plot in FIG. 5 indicates the hole depth increase that would account for the measured cuttings mass (and volume) and that corresponds to a certain measured depth change.

The mass of cuttings coming out of the wellbore should equal the mass of the hole drilled or reamed plus the drilling fluid while accounting for the delay time between drilling and complete cuttings transport from the wellbore. The delay time can be determined by considering the flow rate and/or the transport efficiency of the cuttings. Thus, the cuttings transport calculations can be calibrated in hydraulic models such as drilling simulators. The modelling accuracy can be improved in a manner that impacts ROP optimization.

Figure 6:
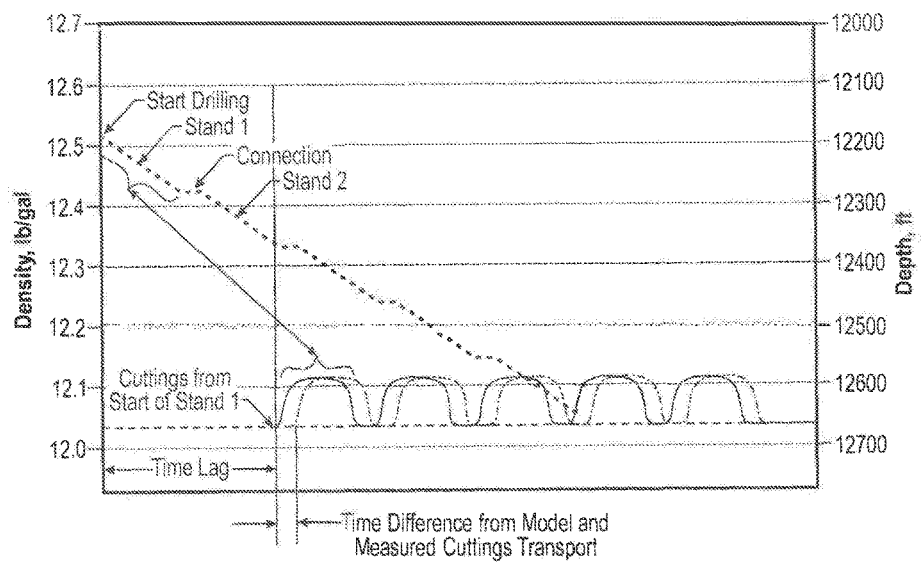
FIG. 6 is a chart showing a correlation between the drilling process, expected density measurement, and theoretical density estimated from a drilling simulator, according to some embodiments.

The theoretical time based curves for cuttings generated can be compared to the time based density curves from the sensor. An exemplary plot is shown in FIG. 6. Drilling in multiple phases is conducted at increasing depth (dotted line). Each phase is separated from adjacent phases by a time in which no cuttings are generated. The measured density (dashed line) from a sensor are compared to a theoretical density (solid line) of a drilling simulator. The periodic nature of the plots is an indication that, for some time after each connection, no hole was drilled, yet some pumping and hole cleaning was done. The periodicity and shape function of the density signatures will follow the operation workflow.

As can be seen in FIG. 6, a time lag occurs between the start of a drilling phase and the theoretical and actual detection of cuttings. Furthermore, a time difference exists between the theoretical detection of cuttings and the actual detection of cuttings. The time difference represents a target parameter for the calibration procedure based on the theoretical model. Since temperature of the vibrating device is measured, the drilling simulator can use a measured temperature as a boundary condition for the thermal models to calibrate the average thermal diffusivity of the formation. The calibration can be performed continuously, periodically, or in real time. The temperature impacts the density and rheology of the fluid and therefore impacts the transport modeling. It will be recognized that calibrating the model's transport efficiency can effectively calibrate for uncertainty.

Using the measurement data facilitates calibration and/or tuning of cuttings transport models in real time. The density measurements are related to the cuttings mass generated by drilling as the mass flow through the sensor. Thus, the density measurements can be used to calibrate the modelled cutting. The integral of the change of density observed at the flow pipe is directly proportional to the cuttings mass generated by drilling in a given time window.

Lost circulation and fluid loss can impact the mass of the system. Part of a mass flux integral can include a comparison of what was pumped at surface to what came out of the hole. Differences can be accounted for in the calculations. Additionally, samples can be taken at multiple locations (e.g., on the surface and downhole) to provide data for comparing the mass flux at the flow line to the mass flux after the shakers.

In some operations, the system can identify the presence of product additions that routinely occur. For example, calculations can consider lost circulation products that are known to be screened out or partially screened out by the shakers.

In some operations, objects (e.g., pills) can be pumps, where the objects have different densities and or viscosities. A system can detect when each pill clears the hole and how efficient the pill was at aiding transport efficiency. If the pill was more efficient than the drilling fluid itself, then a higher average density swept from the hole can be observed, as compared to that of the drilling fluid transporting the cuttings. Other materials can be added to the system periodically depending on the fluids properties. A system and inventory management system can be used during operation.

Ground-up cuttings typically increase the mud weight as well as increase the fluid viscosity. By examining both density and viscosity, the technique can reveal whether cuttings are ground up. For examples, a smooth increase in both density and viscosity would indicate cutting are ground up.

The subject technology can be used to characterize wellbore cleanup during completion operations. Models can be used to predict the density of the spacer packages with the interface mixing down hole and the bulk fluid density exiting the wellbore. In some cases, a mass integral will indicate how much residual drilling fluid was removed from the wellbore.

A method to calibrate the transport efficiency for each annular section can include consideration of the diameter, length, flow rate, and transport efficiency for each annular section. The transport efficiency of cuttings within a fluid is the ratio of the velocity of the cuttings to the velocity of the fluid. The difference between an actual transport efficiency and a modelled transport efficiency can introduce a margin of error in cuttings transport modelling.

The transport efficiency calculated for each section can be modified by a tuning factor calculated by comparing the actual time lag to the theoretical time lag with a running average of the tuning factor being calculated and recorded.

Thus, the trending values of the transport efficiency correction factor can be used to help predict the transport efficiency and minimize the transport error.

Transport efficiency can drive the temporal position of the cuttings. Transport efficiency can be calculated in the model based on size, density, and/or shape of the cuttings, pipe rotation (RPM), fluid viscosity, density corrected for temperature and pressure down hole (applying a heat transfer model), inclination angle, pump rate, and/or annular size. Pump rate, RPM, and heat transfer may not be constant, and fluid parameters can change with operational conditions. Cuttings can settle when the pump rate is insufficient to carry the cuttings. The model described herein can discretely include these considerations during connections and other times when not pumping. For example, the system can model the position of the cuttings discretely, such that in the simulation many volume elements of cuttings are modeled while drilling (i.e., as a discrete element approach, rather than a bulk transport efficiency for all the cuttings in the wellbore). Therefore, each discrete element will have a different transport efficiency based on all the above conditions. With this modeling approach coupled with the actual measurements at the surface, the system can address some of the issues with gas and liquid influx. This can be applied to managed pressure drilling (MPD), where the likelihood of influx is greatest, as well as conventional drilling.

A numerical expression to calculate the volume of cuttings and drilling fluid that pass through the sensor (considering the sensor as one volume element) may be expressed as $$V_i = Q_i \times t_i, \qquad \text{(Eq. 7)}$$

and the total volume for n time elements is $$V = \sum_1^n V_i, \qquad \text{(Eq. 8)}$$

where:
$Q_i$=Average volume flow rate for time element i
$t_i$=Elapsed time for element i.
For each $t_i$ a cuttings volume fraction of the $i^{th}$ element may be calculated by $$V_{fci} = 1 + \frac{(D_c - D_i)}{(D_m - D_c)}, \qquad \text{(Eq. 9)}$$

where:
$D_i$=Measured density of fluid at $t_i$
$D_m$=Drilling fluid density without cuttings
$D_c$=Cuttings density.
The measured density relates to the volume of cuttings. The model can use volume elements. Thus, the model calculates when the volume elements will be going out of the system, for example continuously and in real time. Corresponding density measurements can be taken. The total volume of cuttings after n time elements may be calculated by $$V_c = \sum_1^n \left[\left(1 + \frac{(D_c - D_i)}{(D_m - D_c)}\right)V_i\right]. \qquad \text{(Eq. 10)}$$

The volume of mud after n time elements may be calculated by $$V_m = \sum_1^n \left[\left(\frac{-(D_c - D_i)}{(D_m - D_c)}\right)V_i\right]. \qquad \text{(Eq. 11)}$$

In real time operations, $V_c$ can be related directly to the length of hole drilled and will provide some indication of the amount of ground-up cuttings that have become part of the mud system by trending $D_m$ with time. The length of the hole drilled may be approximated by $$L = \frac{4V_c}{\pi D_h^2}, \qquad \text{(Eq. 12)}$$

where:
$D_h$=Hole diameter
L=Length of drilled hole section
$V_c$=Total cuttings volume after n time elements Accordingly, the cuttings transport can be monitored and the transport relationships within a drilling simulator can be refined.

According to some embodiments, the systems and methods described herein can detect wellbore cavings. When a wellbore caving occurs, debris, which is not a result of cutting with the drill, are generated and enter the circulating fluid. The sensors and processes described herein can detect such debris. Where such detections are outside an expected range based on drilling, a wellbore caving can be inferred. Such a detection can be recorded and transmitted to a user or a program. Predefined alerts and actions can be performed based on the detection. Furthermore, measuring the caving volume can facilitate an estimate of new open-hole diameters that will impact ECD.

According to some embodiments, the systems and methods described herein can be used to evaluate cleanup operations. During a well cleaning method, drilling ceases, so new cuttings are not produced. This change in concentration of cuttings changes the ECD for that portion of the drilling fluid. The cuttings and other debris that are removed from the well can be tracked with the systems and methods described above. Accordingly, it can be detected when cleanup operations have stopped removing mud, cuttings, and other debris from the wellbore. Such a detection can be recorded and transmitted to a user or a program. Predefined alerts and actions can be performed based on the detection.

According to some embodiments, the systems and methods described herein can provide an indication for formation gases in the drilling fluid as an early kick detection method. In this method, using one sensor element will allow the real time system to detect when a gas bubble has gone through the sensor. Since the sensor can detect the mass moving through the sensor, the volume of the gas bubble can be measured or calculated based on flow line volume flow rate, temperature, and/or pressure. The expansion rate of the gas bubble at these conditions can be solved.

For gas kicks, the system can disregard gas dissolved in mud by applying teh formula $$\rho = \rho_m \cdot \varphi_m + \rho_g \cdot (1-\varphi_m), \quad (Eq. 13)$$

where:
$\rho_m$=Mud density
$\rho_e$=Gas density
$\varphi_m$=Mud volume fraction
$(1-\varphi_m)$=Gas volume fraction Thus, gas volume fraction due to gas kick can be estimated from density measurements. By integrating the calculation over time, the total volume of gas in a period of time can be determined. The impacts of both temperature and pressure can be considered. Furthermore, gas solubility can be factored for particular mud systems (e.g., base fluid) by assuming that the fluid is saturated and has a bubble present at the lower pressure than downhole conditions present in the flow line. Based on these assumptions, the total gas volume at standard temperature and pressure can be calculated.

In addition to predicting the expansion rate, two or more sensors can be used in series with an orifice plate between them to sequentially drop the pressure in each element. Then comparing the sensors responses we can further refine the gas volume/mass.

According to some embodiments, an initial model generated by a drilling simulator can be calibrated as described above, and an adjusted model can be generated. Drilling operational parameters can be implemented based on the adjusted model.

For example, the resultant ECD profile of the adjusted model can be compared to the fracture gradient of the subterranean formation. Then, at least one operational parameter (e.g., drilling parameters, fluid parameters, and the like) can be changed based on the comparison. For example, if the ECD is too close to the fracture gradient, the rate of penetration can be reduced, the mud weight can be reduced, the flow rate of the fluid can be decreased, and any combination thereof. By further example, if the ECD is sufficiently far from the fracture gradient, operational parameters like rate of penetration and mud weight can be changed to more efficiently drill the wellbore with an ECD close to the fracture gradient. One skilled in the art would recognize the plurality of operational parameters that can be manipulated and how to manipulate such operational parameters to achieve a desired change in ECD.

In some instances, a transient model for calculating cuttings distribution along the wellbore can be utilized in a predictive method. Similar to above, an ECD profile can be calculated. Additional inputs of theoretical changes to the operational parameters can be used to calculate (e.g., with a drilling simulator) a plurality of predicted ECD profiles that can be used analyzed when choosing an operational parameter change.

Examples of suitable drilling simulators can include DFG RT™ Drilling Fluids Graphics Software (available from Halliburton Energy Services, Inc.) adapted to include inputs from the transient model of the cuttings distribution, real-time data collected during drilling, and/or data collected from a previous drilling operation into the subterranean formation.

Examples of operational parameters that can be changed based on the ECD profile or the predicted ECD profile can include, but are not limited to, flow rate of the drilling fluid, viscosity of the drilling fluid, density (or weight) of the drilling fluid, lubricity of the drilling fluid, fluid composition (e.g., oil based mud vs water or emulsion muds or additives in the fluid), revolutions per minute of the drill bit, rate of penetration into the subterranean formation, torque applied to the drill string, trajectory of the drill bit (e.g., which can change measured depth and true vertical depth), weight on bit, wellbore pressure (e.g., with managed pressure drilling), and the like, and any combination thereof. For example, if the ECD profile or predicted ECD profile is close to the fracture gradient, operational parameters can be changed to reduce the ECD profile (e.g., reduce mud weight, lower the flow rate, lower the rate of penetration, and lower the viscosity of the mud). In another example, to reduce the ECD profile, drilling can be stopped to clean the wellbore.

In some instances, an operator can provide the inputs to the drilling simulator as to the operational parameter changes to be modeled. For example, each operational parameter (or a subset thereof) can have an upper and lower limit and an analysis increment that can be input by an operator, such that the drilling simulator can predict the ECD profile iteratively based on the values between the upper and lower limits at the analysis increments. For example, the effect of the rate of penetration on the ECD can be analyzed between a 5% reduction to 5% increase at 1% increments based on the present rate of penetration. In some instances, the results can be displayed for an operator to determine if the change should be implemented. In some instances, the drilling simulator can automatically implement the changes where the operator has optionally included limits as to the extent of the changes that can be automatically implemented. For example, the rate of penetration can be analyzed as described above and implemented automatically where the operator has included limits as to the absolute values of the rate of penetration. The drilling simulator can alert the operator as to if the operational parameter should be adjusted to outside the operator's limits, so that the operator can decide to adjust such limits. One skilled in the art with the benefit of this disclosure would recognize that this example can be extended to other parameters described herein and combinations of two or more parameters.

In some instances, collecting real-time data, calculations, and calibrations can be performed continuously, at specific time intervals, on-demand by an operator, or a hybrid thereof. For example, real-time data, like revolutions per minute of the drill bit and rate of penetration into the subterranean formation, can be collected continuously, while real-time data, like temperature, is collected periodically (e.g., at specific time intervals or on-demand by the operator). In another example, a hybrid can be employed where an ECD profile is calculated continuously or at specific time intervals and a predicted ECD profile is calculated at specific time intervals or on-demand by an operator. For example, if drilling is occurring such that the ECD can be increased, a predictive model can be used to determine which operational parameters to manipulate to achieve a desired change in ECD.

By engaging in the mathematical and statistical analysis that combine data sources, especially real-time data and transient modeling, the exemplary embodiments described herein can develop ECD profiles and projected ECD profiles along the wellbore as any number of operational parameters are manipulated or theoretically manipulated. This provides more accurate information to the operator so that drilling can be more efficient with less risk of formation fracture and lost circulation.

In some embodiments, the steps of collecting the real-time data, calculating the cuttings distribution, calculating the plurality of predicted ECD profiles, calibrating a drilling model, optionally inputting theoretical changes, and optionally changing the operational parameters can be operated under computer control, remotely and/or at the well site. In some embodiments, the computer and associated algorithm for each of the foregoing can produce an output that is readable by an operator who can manually change the operational parameters.

It is recognized that the various embodiments herein directed to computer control and artificial neural networks, including various blocks, modules, elements, components, methods, and algorithms, can be implemented using computer hardware, software, combinations thereof, and the like. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the scope of the embodiments expressly described.

Computer hardware used to implement the various illustrative blocks, modules, elements, components, methods, and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), erasable read only memory (EPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a "machine-readable medium" refers to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

In some embodiments, the data collected during a drilling operation can be archived and used in future operations. In addition, the data and information can be transmitted or otherwise communicated (wired or wirelessly) to a remote location by a communication system (e.g., satellite communication or wide area network communication) for further analysis. The communication system can also allow for monitoring and/or performing of the methods described herein (or portions thereof).

Figure 7:
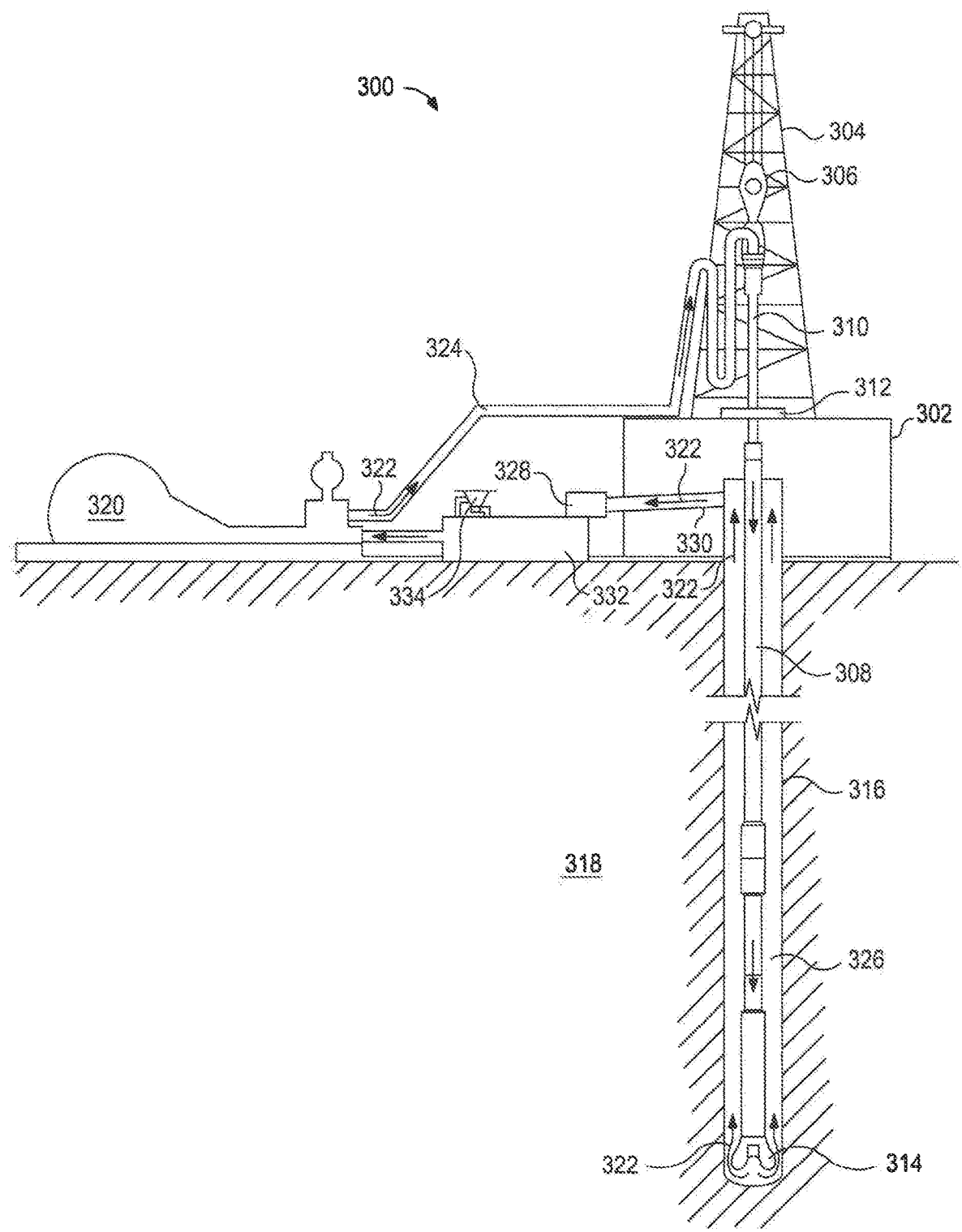
FIG. 7 is a plan view of a drilling assembly suitable for use in conjunction with at least one embodiment described herein.

As illustrated in FIG. 7, some embodiments can include a drilling assembly 300. It should be noted that while FIG. 7 generally depicts a land-based drilling assembly, those skilled in the art will readily recognize that the principles described herein are equally applicable to subsea drilling operations that employ floating or sea-based platforms and rigs, without departing from the scope of the disclosure.

The drilling assembly 300 can include a drilling platform 302 that supports a derrick 304 having a traveling block 306 for raising and lowering a drill string 308. The drill string 308 can include, but is not limited to, drill pipe and coiled tubing, as generally known to those skilled in the art. A kelly 310 supports the drill string 308 as it is lowered through a rotary table 312. A drill bit 314 is attached to the distal end of the drill string 308 and is driven either by a downhole motor and/or via rotation of the drill string 308 from the well surface. As the drill bit 314 rotates, it creates a borehole (or wellbore) 316 that penetrates various subterranean formations 318.

A pump 320 (e.g., a mud pump) circulates wellbore fluid 322 through a feed pipe 324 and to the kelly 310, which conveys the wellbore fluid 322 downhole through the interior of the drill string 308 and through one or more orifices in the drill bit 314. The wellbore fluid 322 is then circulated back to the surface via an annulus 326 defined between the drill string 308 and the walls of the borehole 316. At the surface, the recirculated or spent wellbore fluid 322 exits the annulus 326 and can be conveyed to one or more fluid processing unit(s) 328 via an interconnecting flow line 330. After passing through the fluid processing unit(s) 328, a "cleaned" wellbore fluid 322 is deposited into a nearby retention pit 332 (i.e., a mud pit). While illustrated as being arranged at the outlet of the borehole 316 via the annulus 326, those skilled in the art will readily appreciate that the fluid processing unit(s) 328 can be arranged at any other location in the drilling assembly 300 to facilitate its proper function, without departing from the scope of the scope of the disclosure.

The wellbore fluids 322 can be produced with a mixing hopper 334 communicably coupled to or otherwise in fluid communication with the retention pit 332. The mixing hopper 334 can include, but is not limited to, mixers and related mixing equipment known to those skilled in the art. In other embodiments, however, the wellbore fluid 322 can be produced at any other location in the drilling assembly 300. In at least one embodiment, for example, there could be more than one retention pit 332, such as multiple retention pits 332 in series. Moreover, the retention pit 332 can be representative of one or more fluid storage facilities and/or units where the disclosed individual wellbore fluid components can be stored, reconditioned, and/or regulated until added to the wellbore fluid 322.

One or more sensors, gauges, and the like for measuring the real-time data described herein (e.g., wellbore fluid properties, wellbore conditions relating to a section of the wellbore, operational parameters, and combinations thereof) can be coupled to at least one of the pump 320, the drill string 308, the rotary table 312, the drill bit 314, and the like. The data from these sensors, gauges, and the like can be transmitted (wired or wirelessly) to a computing station that implements calculating cuttings distributions and the like based on at least based on (1) the cuttings distribution and (2) the real-time data and provides an equivalent circulating density profile and the like, which can be used for changing at least one operational parameter based on comparisons and analyses described herein.

FURTHER CONSIDERATIONS

Various examples of aspects of the disclosure are described below as clauses for convenience. These are provided as examples, and do not limit the subject technology.

Clause A. A method comprising: drilling a wellbore penetrating a subterranean formation while circulating a drilling fluid; with a sensor, detecting an actual density of cuttings in the drilling fluid and within a region of a flow pipe, the cuttings being formed by the drilling; calculating a modelled density of the cuttings in the region based on an initial model, wherein the initial model is based on a comparison of an equivalent circulating density profile to a fracture gradient of the subterranean formation; generating an adjusted model based on the initial model and on a comparison of the actual density of the cuttings to the modelled density of the cuttings; and changing at least one operational parameter of the drilling based on the adjusted model.

Clause B. A drilling assembly comprising: a flow pipe for directing a drilling fluid; a sensor coupled to the flow pipe and configured to detect an actual density of cuttings in the drilling fluid and within a region of a flow pipe; and a processor programmed to: calculate a modelled density of the cuttings in the region based on an initial model, wherein the initial model is based on a comparison of an equivalent circulating density profile to a fracture gradient of a subterranean formation; generate an adjusted model based on the initial model and a comparison of the actual density of the cuttings to the modelled density of the cuttings; and change at least one operational parameter of a drilling operation of the drilling assembly based on the adjusted model.

Clause C. A non-transitory computer-readable tangible medium comprising executable instructions that cause a computing device to: while drilling a wellbore penetrating a subterranean formation, while circulating a drilling fluid, and with a sensor, detecting an actual density of cuttings in the drilling fluid and within a region of a flow pipe, the cuttings being formed by the drilling; calculate a modelled density of the cuttings in the region based on an initial model, wherein the initial model is based on a comparison of an equivalent circulating density profile to a fracture gradient of the subterranean formation; generate an adjusted model based on the initial model and a comparison of the actual density of the cuttings to the modelled density of the cuttings; and change at least one operational parameter of the drilling based on the adjusted model.

In one or more aspects, the method, drilling assembly, and/or non-transitory computer-readable tangible medium of any preceding paragraph, either alone or in combination, can further include one or more features of the additional clauses described below.

The adjusted model is based on a comparison of a time when the actual density of the cuttings is measured at a value to a time when the modelled density of the cuttings are expected to be measured at the value.

Detecting the actual density of the cuttings comprises: calculating a resonance frequency of the flow pipe while the cuttings and the drill fluid are within the region; measuring a temperature of the flow pipe; and calculating the actual density of the cuttings based on the resonance frequency and the temperature.

The generating the adjusted model comprises calculating a tuning factor of the adjusted model by comparing an actual time lag of the cuttings arriving at the region to a modelled time lag of the cuttings arriving at the region.

A method also includes calculating a cuttings mass as an integral of a change of the density of the cuttings.

A method also includes adjusting the adjusted model based on a comparison of a running average of values for the actual density of the cuttings to the modelled density of the cuttings.

A method also includes with the sensor, detecting a characteristic of a gas bubble moving through the region; and transmitting an indication of the characteristic to a surface of the subterranean formation.

Detecting the characteristic comprises determining a volume of the gas bubble by comparing measurements of the gas bubble from separate sensors positioned along the flow pipe.

The sensor is further configured to apply vibrational energy to the flow pipe and detect a resonance frequency of the flow pipe.

The sensor is further configured to measure a temperature of the flow pipe.

The sensor comprises a fiber optic device, a metallic wire, a strain gauge, or an electric hammer.

The system also includes an additional sensor coupled to the flow pipe at an additional region; and an orifice plate between the sensor and the additional sensor, the orifice plate having an inner cross-sectional dimension that is smaller than an inner cross-sectional dimension of the region and an inner cross-sectional dimension of the additional region.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A method comprising:
   drilling a wellbore penetrating a subterranean formation while circulating a drilling fluid; with a sensor, detecting an actual density of cuttings in the drilling fluid and within a region of a flow pipe, the cuttings being formed by the drilling, and with the sensor, detecting a characteristic of a gas bubble moving through the region, wherein detecting the characteristic comprises determining a volume of the gas bubble by comparing measurements of the gas bubble from separate sensors positioned along the flow pipe;
transmitting an indication of the characteristic of the gas bubble to a surface of the subterranean formation;
calculating a modelled density of the cuttings in the region based on an initial model, wherein the initial model is based on a comparison of an equivalent circulating density profile to a fracture gradient of the subterranean formation;
generating an adjusted model based on the initial model and on a comparison of the actual density of the cuttings to the modelled density of the cuttings; and
changing at least one operational parameter of the drilling based on the adjusted model.

2. The method of claim 1, wherein the adjusted model is based on a comparison of a time when the actual density of the cuttings is measured at a value to a time when the modelled density of the cuttings are expected to be measured at the value.

3. The method of claim 1, wherein detecting the actual density of the cuttings comprises:
calculating a resonance frequency of the flow pipe while the cuttings and the drill fluid are within the region;
measuring a temperature of the flow pipe; and
calculating the actual density of the cuttings based on the resonance frequency and the temperature.

4. The method of claim 1, wherein the generating the adjusted model comprises calculating a tuning factor of the adjusted model by comparing an actual time lag of the cuttings arriving at the region to a modelled time lag of the cuttings arriving at the region.

5. The method of claim 1, further comprising calculating a cuttings mass as an integral of a change of the density of the cuttings.

6. The method of claim 1, further comprising adjusting the adjusted model based on a comparison of a running average of values for the actual density of the cuttings to the modelled density of the cuttings.

7. A drilling assembly comprising:
a flow pipe for directing a drilling fluid;
a sensor coupled to the flow pipe and configured to detect an actual density of cuttings in the drilling fluid and within a region of a flow pipe, and configured to detect a characteristic of a gas bubble moving through the region wherein detecting the characteristic comprises determining a volume of the gas bubble by comparing measurements of the gas bubble from separate sensors positioned along the flow pipe; and
a processor programmed to:
calculate a modelled density of the cuttings in the region based on an initial model, wherein the initial model is based on a comparison of an equivalent circulating density profile to a fracture gradient of a subterranean formation;
generate an adjusted model based on the initial model and a comparison of the actual density of the cuttings to the modelled density of the cuttings;
change at least one operational parameter of a drilling operation of the drilling assembly based on the adjusted model; and
transmit an indication of the characteristic to a surface of the subterranean formation.

8. The drilling assembly of claim 7, wherein the sensor is further configured to apply vibrational energy to the flow pipe and detect a resonance frequency of the flow pipe.

9. The drilling assembly of claim 7, wherein the sensor is further configured to measure a temperature of the flow pipe.

10. The drilling assembly of claim 7, wherein the sensor comprises a fiber optic device, a metallic wire, a strain gauge, or an electric hammer.

11. The drilling assembly of claim 7, further comprising:
an additional sensor coupled to the flow pipe at an additional region; and
an orifice plate between the sensor and the additional sensor, the orifice plate having an inner cross-sectional dimension that is smaller than an inner cross-sectional dimension of the region and an inner cross-sectional dimension of the additional region.

12. A non-transitory computer-readable tangible medium comprising executable instructions that cause a computing device to:
while drilling a wellbore penetrating a subterranean formation, while circulating a drilling fluid, and with a sensor, detecting an actual density of cuttings in the drilling fluid and within a region of a flow pipe, the cuttings being formed by the drilling, and with the sensor, detect a characteristic of a gas bubble moving through the region wherein detecting the characteristic comprises determining a volume of the gas bubble by comparing measurements of the gas bubble from separate sensors positioned along the flow pipe;
transmit an indication of the characteristic to a surface of the subterranean formation;
calculate a modelled density of the cuttings in the region based on an initial model, wherein the initial model is based on a comparison of an equivalent circulating density profile to a fracture gradient of the subterranean formation;
generate an adjusted model based on the initial model and a comparison of the actual density of the cuttings to the modelled density of the cuttings; and
change at least one operational parameter of the drilling based on the adjusted model.

13. The non-transitory computer-readable tangible medium of claim 12, wherein the adjusted model is based on a comparison of a time when the actual density of the cuttings is measured at a value to a time when the modelled density of the cuttings are expected to be measured at the value.

14. The non-transitory computer-readable tangible medium of claim 12, wherein detecting the actual density of the cuttings comprises:
calculating a resonance frequency of the flow pipe while the cuttings and the drill fluid are within the region;
measuring a temperature of the flow pipe; and
calculating the actual density of the cuttings based on the resonance frequency and the temperature.

15. The non-transitory computer-readable tangible medium of claim 12, wherein generating the adjusted model comprises calculating a tuning factor of the adjusted model by comparing an actual time lag of the cuttings arriving at the region to a modelled time lag of the cuttings arriving at the region.

16. The non-transitory computer-readable tangible medium of claim 12, wherein the instructions further cause the computing device to calculate a cuttings mass as an integral of a change of the density of the cuttings.

17. The non-transitory computer-readable tangible medium of claim 12, wherein the instructions further cause the computing device to adjust the adjusted model based on a comparison of a running average of values for the actual density of the cuttings to the modelled density of the cuttings.

\* \* \* \* \*